(12) United States Patent
Lin et al.

(10) Patent No.: US 8,207,403 B2
(45) Date of Patent: Jun. 26, 2012

(54) EPSP SYNTHASE WITH HIGH GLYPHOSATE RESISTANCE AND ITS ENCODED SEQUENCE

(75) Inventors: Min Lin, Beijing (CN); Aimin Liang, Beijing (CN); Wei Lu, Beijing (CN); Liang Li, Beijing (CN); Ming Chen, Beijing (CN); Wei Zhang, Beijing (CN); Shuzhen Ping, Beijing (CN)

(73) Assignee: Biotechnology Research Institute The Chinese Academy of Agricultural Sciences, Beijing (CN)

( * ) Notice: Subject to any disclaimer, the term of this patent is extended or adjusted under 35 U.S.C. 154(b) by 112 days.

(21) Appl. No.: 12/741,965

(22) PCT Filed: Nov. 16, 2007

(86) PCT No.: PCT/CN2007/071071
§ 371 (c)(1),
(2), (4) Date: Jul. 13, 2010

(87) PCT Pub. No.: WO2009/059485
PCT Pub. Date: May 14, 2009

(65) Prior Publication Data
US 2011/0173716 A1    Jul. 14, 2011

(30) Foreign Application Priority Data
Nov. 9, 2007  (CN) .......................... 2007 1 0177090

(51) Int. Cl.
*C12N 9/10* (2006.01)
*C12N 15/52* (2006.01)
*C12N 15/63* (2006.01)
*C12N 15/82* (2006.01)

(52) U.S. Cl. ..... 800/300; 435/193; 435/419; 435/320.1; 536/23.2; 800/288

(58) Field of Classification Search ....................... None
See application file for complete search history.

(56) References Cited

U.S. PATENT DOCUMENTS
7,960,615 B2 * 6/2011 Peters et al. ................. 800/300

FOREIGN PATENT DOCUMENTS
| CN | 1664095 A | 9/2005 |
| CN | 1952152 A | 4/2007 |
| WO | WO2007064828 A | 6/2007 |

* cited by examiner

*Primary Examiner* — David H Kruse
(74) *Attorney, Agent, or Firm* — Drinker, Biddle & Reath, LLP (57) ABSTRACT

An EPSP synthase (5-enolpyruvylshikimate-3-phosphate synthase) with high glyphosate resistance and a nucleotide sequence encoding the synthase are disclosed. The gene encoding the EPSP synthase has low homology with the reported EPSP synthase. A transgenic plant obtained by the expression of the gene in plant has an increased resistance to glyphosate after experimental confirmation.

6 Claims, 2 Drawing Sheets

EPSP SYNTHASE WITH HIGH GLYPHOSATE RESISTANCE AND ITS ENCODED SEQUENCE

FIELD OF THE INVENTION

The invention relates to a new EPSP synthase (5-enolpyruvylshikinate-3-phosphate synthase) with high glyphosate resistance, and a nucleotide sequence encoding such synthase.

BACKGROUND OF THE INVENTION

Glyphosate is the main active component in Roundup®, which is a product from Monsanto Co., Ltd. It is a kind of broad spectrum, translocated and excellent herbicide and it is one of the herbicides widely used. However, it is also a non-selective herbicide and it may kill the crop as well. It is desirable to breed a crop with glyphosate resistance or degradation property in order to use glyphosate in the agricultural production.

Glyphosate inhibits the activity of 5-enolpyruvylshikinate-3-phosphate synthase (EPSP) in the Metabolic process of shikimic acid, and thus blocks the biosynthesis of aromatic amino acids, which leads to the death of the plant (S. R. Padgette et al., in. *Herbicide-Resistance Crops: Agricultural, Environmental, Economic, Regulatory, and Technical Aspects*, S. O. Duke, Ed. (CRC Press; Boca Raton, Fla., 1996), pp. 53-84). Currently, all the transgenic plants with glyphosate resistance commercially grown in the world are designed in allusion to EPSP, which is the only mechanism of action of commercial transgenic plants with glyphosate resistance AroA mutants were obtained using chemical mutagenesis of bacteria, and it was confirmed that aroA gene was the encoding gene for EPSP synthase which is the action target of glyphosate through the study of mechanism of drug resistance. More than 100 patents in the field of encoding gene aroA for EPSP synthase and the transgenic plants with glyphosate resistance had been filed by many companies such as Monsanto and Calgene in USA, and a series of transgenic crops with glyphosate resistance had been obtained, such as soybean, corn, *brassica*, sweet beet and cotton, wherein many transgenic crops including soybean had been commercially produced.

Up to now, there is no report about EPSP synthase which has glyphosate resistance and lower homology with the reported encoding gene of EPSP synthase (aroA) at nucleotide level.

SUMMARY OF THE INVENTION

Objects of the invention are to find and artificially synthesize a new EPSP synthase with high glyphosate resistance and a nucleic acid sequence encoding such synthase, further to transform the sequence into a plant to breed a transgenic plant with high glyphosate resistance.

Figure 3:
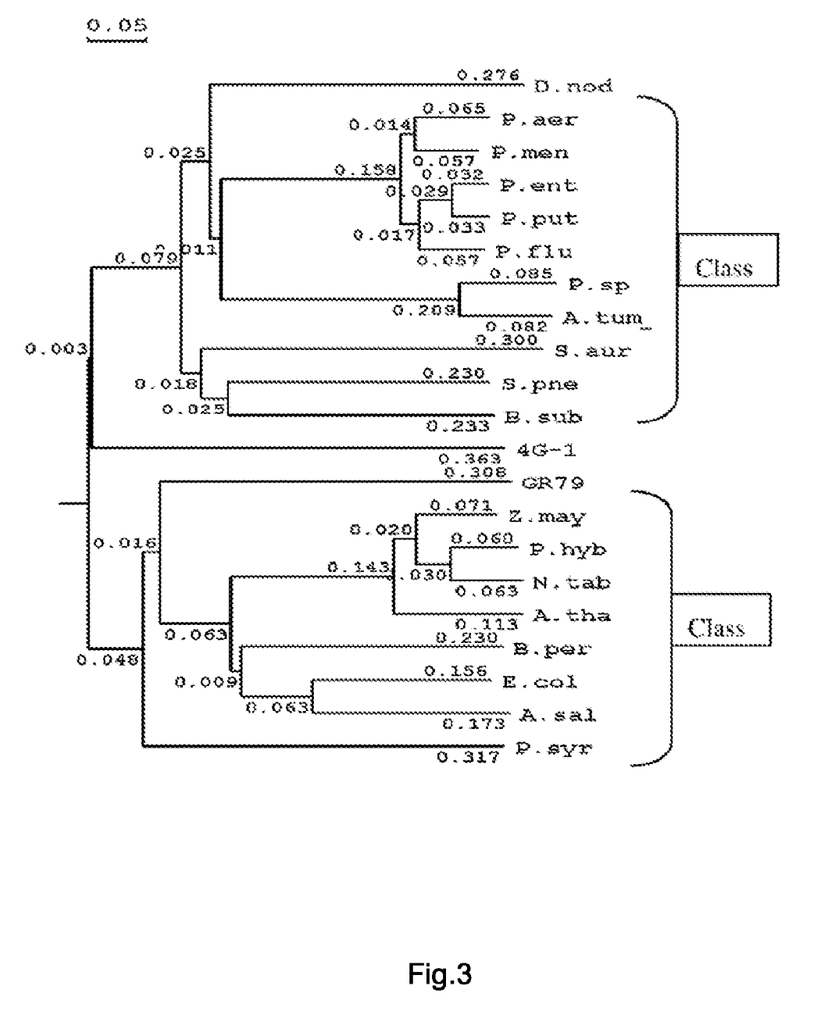
FIG. 3 is the comparison of the amino acid sequence of GR-79 with that of the typical Class and Class II reported.

The inventors firstly found a new EPSP synthase with high glyphosate, the amino acid sequence is set forth in SEQ ID NO:1, and the nucleic acid sequence encoding the synthase is set forth in SEQ ID NO:2 or SEQ ID NO:3. It shows that the EPSP synthase belongs to type I EPSP synthase through the analysis of sequence structure and sequence alignment (see FIG. 3).

The soil samples of environment extremely contaminated with glyphosate were collected, the total DNA at community level was isolated from the samples by free culturing method, the total DNA cosmid library at community level was constructed and the transformants with glyphosate resistance were screened; the transformants were dotted onto M9 solid medium with 20 mM glyphosate to screen the transformants with resistance. The glyphosate tolerance test was also performed and the result showed that the transformants as described above had very strong activity of glyphosate resistance.

The complete nucleotide sequence of DNA fragment with high glyphosate, resistance was determined. The result showed that the size of insert was 3151 bp, wherein it contained a reading frame of 1335 bp, the sequence of which was set forth in SEQ ID NO:2, the full length of the nucleotide sequence which contained was 1335 bp, and the open reading frame was located at 885-2220 and encoded EPSP synthase, the full length of which was 445 amino acids (as set forth in SEQ ID NO:1).

The EPSP synthase gene with high glyphosate resistance as described above was artificially synthesized and the sequence of the synthase was set forth in SEQ ID NO:3. The EPSP gene artificially synthesized with enzyme cutting sites BamHI, and HindIII at 5' and 3' ends Was used to express EPSP synthase with high glyphosate resistance and construct the plant expression vector of the corresponding gene. The EPSP gene artificially synthesized as described above was cut with BamHI and HindIII, and then was ligated to the vector pET28a cut with the same enzymes to give the recombinant vector pETGR-79 which would be used to transform *E. coli* BL21 (DE3) (Promega Company).

The enzyme activity and kinetic parameters of EPSP synthase were also determined, the enzyme activity Was 10.477 U/mg and $K_i/K_m$ was 2.16. From the kinetic parameters, GR-79 EPSP not only had higher glyphosate resistance, but also retained stronger affinity to PEP. These properties provided the possibility to breed the transgenic crops.

The plant expression vector of EPSP synthase gene with high glyphosate resistance was constructed and transgenic tobaccos were constructed by transformation using leaf disc cocultivation. It proved that the transgenic plants could grow well in the medium, with 20 mM glyphosate through glyphosate resistance gradient assay.

The invention also provides a recombinant vector, which contains DNA of SEQ ID NO: 2. The host cells are transformed with the recombinant vectors as described above and the host cells include prokaryotic cells and eukaryotic cells.

The invention also provides a method for introducing SEQ ID NO:2 into a plant using transgenic technique to improve glyphosate resistance of the plant, which comprises the steps:

(1) The sequence set forth in SEQ ID NO: 1 or SEQ ID NO: 2 is operatively linked to the regulation sequence of plant expression to form a plant expression vector;

(2) The expression vector of the step (1) is introduced into the plant cells;

(3) The transformed cells are obtained via screening and they are ultimately regenerated into the transgenic plants and progenies thereof, including seeds and tissues of the plants.

The term "operatively linked to" as described above means that such linkage allows certain regions of a linear DNA sequence to be capable of having an influence on the activity of the remaining regions of the same linear DNA sequence. For example, DNA of signal peptide (secretion leader sequence) is operatively linked to DNA of polypeptide if DNA of signal peptide is expressed as precursor and participates in the secretion of the polypeptide; the promoter is operatively linked to the coding sequence if it controls the transcription of the sequence; the ribosome binding site is operatively linked to the coding sequence if it is located at the position making it be translated. In general, the term "operatively linked to" means to be adjacent and to be adjacent in reading frame for the secretion leader sequence.

The vectors as described above may be selected from various vectors known in the art, such as commercially available vectors including plasmid, cosmid and the like.

In the invention, the encoding sequence of EPSP synthase refers to the nucleotide sequence of polypeptide with protein activity of SEQ ID NO:1 and the degenerate sequence thereof. The degenerate sequence refers to the sequence where one or more codons are substituted with degenerate codons coding the same amino acid. The degenerate sequence with as low as about 89% homology with SEQ ID NO:2 can also code the sequence of SEQ ID NO:2 due to the degeneracy of the codons. The term also includes the nucleotide sequence hybridized with the nucleotide sequence of SEQ ID NO:2 under moderate stringent conditions, preferably high stringent conditions. The term further includes the nucleotide sequence with at least 89% homology with the nucleotide sequence of SEQ ID NO: 2, preferably at least 80%, more preferably at least 90%, most preferably at least 95%.

The term also includes variants of the open reading frame sequence of SEQ ID NO:2, which are capable of encoding the proteins with the same function as natural SEQ ID NO: 1. These variants include, but are not limited to, the deletion, insertion and/or substitution of several nucleotides, generally, 1-90, preferably 1-60, more preferably 1-20, most preferably 1-10 nucleotides, as well as the addition of several nucleotides, generally less than 60, preferably less than 30, more preferably less than 10, most preferably less than 5 nucleotides, at 5' and/or 3' end thereof.

In the invention, the protein of SEQ ID NO: 1 also includes the variants with the same function as SEQ ID NO:1. The variants include, but are not limited to, the deletion, insertion and/or substitution of several amino acids, generally 1-50, preferably 1-30, more preferably 1-20, most preferably 1-10 amino acids, as well as the addition of one or more amino acids, generally less than 20, preferably less than 10, more preferably less than 5, at C and/or N terminus thereof. For example, in the said protein, the function of the protein is generally not changed when substitution is carried out using the amino acids functionally similar or resembling. Another example shows the function of the protein generally may not be changed by adding one or more amino acids at C-terminus and/or N-terminus. The term also includes the active fragments or active derivatives of the protein of SEQ ID NO: 1.

The said variants of the polypeptide include: homologous sequences, conservative variant polypeptides of EPSP synthase, allelic variants, natural variants, inducted variants, proteins encoded by DNA hybridized with SEQ ID NO:2 under high or low stringent conditions and polypeptides and proteins obtained by using antiserum of SEQ ID NO:1 polypeptide.

"Conservative variant polypeptides of EPSP synthase" refer to the polypeptides having at most 10, preferably at most, 8, more preferably at most 5 amino acids substituted with amino acids with resembling or similar properties compared to the amino acid sequence of SEQ ID NO:1. The conservative variant polypeptides are prepared by the substitutions of amino acids according to table 1 as below.

TABLE 1

| Original residue | amino acid substitution | |
|---|---|---|
| | Representative substitution | Preferred substitution |
| Ala (A) | Val; Leu; Ile | Val |
| Arg (R) | Lys; Gln; Asn | Lys |

TABLE 1-continued

| Original residue | amino acid substitution | |
|---|---|---|
| | Representative substitution | Preferred substitution |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

BRIEF DESCRIPTION OF THE DRAWINGS

CP4-ER strain was a strain with glyphosate resistance obtained by ligating the EPSP synthase gene from *Agrobacterium* sp. cp4 to the vector pACYC 184 and introducing into EPSP synthase defective *E. coli* ER2799 strain (NEB Company). It was used as a positive control in the figure.

pACYC184-ER was EPSP synthase defective *E. coli* ER2799 strain containing the vector pACYC184 (NEB Company). It was used as a negative control in the figure.

The three strains were respectively inoculated into the limited medium M9 with the glyphosate concentration of 0, 20, 50, 80, 100, 120, 150, 200, 250, 300 mM, shaking cultured at 37° C. for 36 h, the absorbance values were determined at OD600 and the figure was plotted with the values.

From the figure, the strain GR-79-ER could grow in the limited medium with 250 mM glyphosate and it indicated that the glyphosate resistance of the strain could be up to 250 mM. It indicated that the exogenous fragments carried by plasmid were functionally complementary to the defective strain ER2799 However, the negative control strain could not grow in the limited medium and was not functionally complementary to the defective strain. The glyphosate resistance of the positive control strain could be up to 200 mM.

The EPSP synthase gene of GR-79 strain was ligated to the vector pET28a and then was introduced into BL21. The expression of the protein was induced with IPTG and the samples were taken at one-hour interval. The samples were boiled and isolated by SDS-PAGE electrophoresis. The result showed that the amount of the protein expression of the strain had achieved a higher level within 4 hours. The protein expressed was a soluble protein and the size was about 45 kD.

The result of comparison showed that the amino acid sequence of GR-79 belonged to EPSP synthase of Class I, and the EPSP synthase of GR-79 was a type I enzyme with glyphosate resistance.

THE EMBODIMENTS

The invention will be further described by following examples. It should be understood that the examples are intended to illustrate the methods of the invention and are not intended to limit the scope of the invention. All experiment conditions not described are according to the conventional conditions well known in the art.

Example 1

Cloning of DNA Fragment with High Lyphosate Resistance

1. Collecting the Samples from the Soil Extremely Contaminated with Glyphosate

The samples were collected from the soil contaminated with about 50% glyphosate for more than 10 years (in a certain chemical industrial Co., Ltd in Hebei, China).

2. Isolation of Total DNA at the Community Level from the Soil Extremely Contaminated with Glyphosate Using Free Culturing Method 2 g of the soil were weighted and added with 0.6 g of small glass beads (d<0.11 mm), and shook at 4000 rpm twice. 300 µl SDS, 12% phenol-Tris buffer (pH8.0) were added and the solution was frozen for one hour. An equal volume (about 700 ml) of phenol-Tris buffer (pH8.0) was added, mixed well and then centrifuged at 13,000 rpm for 5 min. 0.1× volume of 3M NaAc (pH 5.2) was added, into the supernatant, mixed well, and subsequently added 0.6× volume of isopropanol and mixed. The DNA pellet (crude DNA) was dissolved in 200 µl 1×TE buffer. 100 mg CsCl was weighted and added into a new 1.5 ml Epp.tube, gently mixed with 100 µl crude DNA, and incubated in the dark for 1-3 hours. The solution was centrifuged at 13,000 rpm for 20 min at room temperature. 400 µl sterile de-ionized water and 300 µl isopropanol were added to the supernatant, and kept at room temperature for 30 min. The solution was centrifuged at 13,000 rpm for 20 min at room temperature. The pellet was dissolved in the mixture of 100 µl 1×TE buffer and 40 µl 8M KAc, and kept at room temperature for 15 min. The solution was centrifuged at: 13,000 rpm for 15 min at 4° C. The supernatant was mixed with 0.6× volume of isopropanol, and kept at room temperature for 30 min. The solution was centrifuged at 15,000 rpm for 20 min at room temperature. The DNA pellet was dissolved in 100 µl 1×TE.

The DNA samples were purified using Wizard spin column clean-up isolation kit. The purified DNA was dissolved in 10 mM Tris-EDTA (pH8.0) buffer with the total volume of 100 µl.

3. Construction of the Total DNA Cosmid Library at Community Level

The DNA, of soil bacteria was cut with Sau3AI of 1:100 dilution in 10 µl of reaction system at 37° C. for 10, 20, 30, 40, 50, 60 min respectively, and then 1 µl of 10× loading buffer was added to end the reaction. The optimal reaction time was determined by electrophoresis. The same enzyme system was selected to cut for 30 min in a large scale. 2-6 kb DNA fragments were recovered by excising after agarose gel electrophoresis for the further use. The plasmid vector pACY184 (NEB company) was fully cut with BamHI and then the dephosphorylation was performed with SAP alkaline phospholipase to reduce the self-ligation of the vector. The DNA of soil bacteria (200 ng) and the plasmid vector pACYC184 dephosphorylated terminally were ligated with 2U T4 ligase at 4° C. for 16 h.

The ligated product as described above was introduced into *E. coli* ER2799 (NEB Company) shock competent cells, and the cells were plated onto LB+Cm$^r$. The clones grown on the LB plates were printed onto the plates with M9+Cm$^r$+50 mM glyphosate and cultured at 37° C. for 48 h. The bacteria on the plates were cultured through streak culture on the LB plates and then the colonies were reseeded onto the M9 plates with glyphosate of different concentration (100, 150 mM glyphosate). The plasmids in the recombinant strains were exacted and used to transform the ER2799, and then they were plated onto the M9+Cm$^r$ plates for confirmation (ER2799+pA-CYC184 as control), and the confirmation with enzymatic cutting of the recombinant plasmids was performed.

4. Screening of Transformants with Glyphosate Resistance

The transformants were plated onto LB plates with Cm (chloromycetin) and cultured at 37° C. for 20 h. There were about 5000 clones growing on the plates, the clones were printed onto the plates with Cm$^r$ and 50 mM glyphosate and cultured for 48 h, three clones grew up. These three clones were inoculated to M9 plates with 100 mM or 150 mM glyphosate respectively, only one, clone could grow on M9 plate with 150 mM glyphosate, and the plasmid which contained was named pACYCGR-79. The plasmid pACYCGR-79 extracted from the clone was induced into *E. coli*. ER2799 (NEB Company) or *E. coli* JM109 (Promega Company), the transformants were dotted on M9 solid medium with 20 mM glyphosate using sterile tooth pick, in order to detect the resistance, the result showed that all of the transformants produced by the clones had glyphosate resistance, indicating that the glyphosate resistance was due to the introduction of pACYCGR-79.

5. Glyphosate Tolerance Test

*E. coli* ER2799 (containing new cloned pACYCGR-79 plasmid) was inoculated into M9 liquid medium (Cm$^r$) with 0-200 mm glyphosate, shaking cultured at 37° C. for 36 h, and the OD600 value of culture was determined. *E. coli* ER2799 with plasmid without insert was used as negative control.

Figure 1:
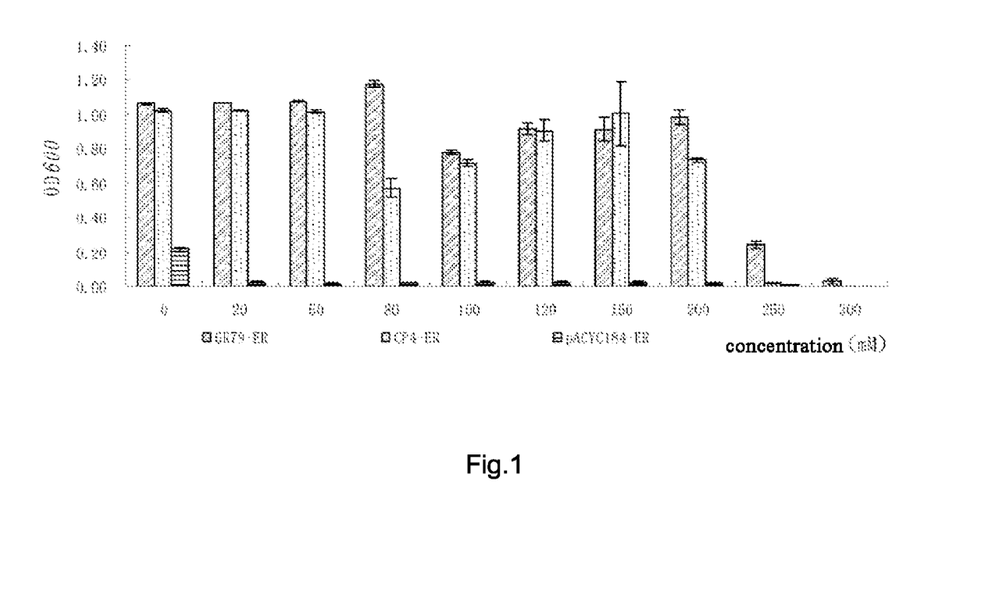
FIG. 1 is a graph of analysis of glyphosate resistance of clone GR-79, wherein: GR-79-ER strain was a strain with glyphosate resistance obtained by cutting the total DNA of soil with enzyme partly, ligating the vector pACYC 184 and introducing into EPSP synthase defective *E. coli* ER2799 strain (NEB Company).

Results: *E. coli* ER2799 (carrying pACYCGR-79plasmid) was inoculated into M9 liquid medium (Cm$^r$) with 0-300 mM glyphosate, shaking cultured at 37° C. for 36 h, it was found that the negative controls could hardly grow in M9; while ER2799 (pACYCGR-79) could even grow in M9 liquid medium with 250 mM glyphosate (see FIG. 1). The result implied that the exogenous fragment carried by pACYCGR-79 had very, strong activity of glyphosate resistance. The positive control strains with CP4 plasmid could only grow in the liquid medium with 200 mM glyphosate.

Example 2

Sequence Analysis of DNA Fragments with High Glyphosate Resistance and Verification, of EPSP Synthase Functions 1. Sequence Analysis of DNA Fragment with High Glyphosate Resistance The complete nucleotide sequence of the DNA fragment with high glyphosate resistance subcloned in example 1 was determined. The results of the analysis showed that the size of the insert fragment was 3151 bp, containing a reading frame with 1335 bp, the sequence of which was set forth in SEQ ID NO.1, the full length of the polynucleotide which contained was 1335 bp, the open reading frame was located at 885-2220 positions, encoding a EPSP synthase with the full length of 445 amino acids.

When the encoding sequence with high glyphosate resistance subcloned was compared with the encoding gene of EPSP synthase (aroA) reported; the homology at nucleotide level was low.

The analytic results of homology of amino acid sequences showed that the homology of the amino acid sequence between GR-79 and typical type I EPSP synthase was higher than that between the enzyme and type II EPSP synthase, and the amino acid sequence of GR79 did not contain the typical conserved amino acid region of type II synthase, while the conserved amino acid region was similar to that of type I synthase. It illustrated that GR-79 EPSP belonged to type I EPSP. The results of phylogeny comparison between GR-79 EPSP and classic type I and II EPSP synthase were shown in FIG. 3.

Example 3

Artificial Synthesis of EPSP Synthase Gene with High Glyphosate Resistance

Basing on the nucleotide sequence containing a coding region of 1335 bp, it was firstly divided into 8 regions, and then the single strand oligonucleotide fragments in 150-200 bp length with cohesive terminus were synthesized according to sequences of the positive strands or the negative strands, respectively. The 8 complementary single strand oligonucleotide fragments corresponding to the positive strands or the negative strands were annealed to form 8 double strands oligonucleotide fragments with cohesive terminus. The double strands oligonucleotide fragments were combined, and assembled catalytically into a whole gene of EPSP synthase via T4 ligase. The DNA fragment synthesized contained the nucleotide sequence of SEQ ID NO:2 at 1-335 positions, and the gene synthesized contained BamHI and HindIII sites at two ends of the upstream and downstream. As shown in SEQ ID NO:2.

The EPSP gene with BamHI and HindIII enzyme cutting sites at 5' and 3' ends as artificially synthesized above was used to express EPSP synthase with high glyphosate resistance and construct a plant expression vector of the corresponding gene.

Example 4

Expression of EPSP with High Glyphosate Resistance

After the EPSP gene with BamHI and HindIII enzyme cutting sites at and 3' ends artificially synthesized as above was enzymatically cut with BamHI and HindiII, the EPSP gene was ligated into vector pET28a (NEB company) cut with the same enzyme to give the recombinant plasmid pETGR-79 which was then used to transform E. coli BL21 (DE3) (Promega company). The transformants were firstly cultured in LB+Km$^r$ medium at 37° C. and 200 rpm until the OD600 value reached about 0.5, IPTG was added (to the final concentration of 0.75 mmol/L) and then the temperature was changed to 37° C. to induce the expression of the protein, and the detection was performed using SDS-PAGE electrophoresis.

Figure 2:
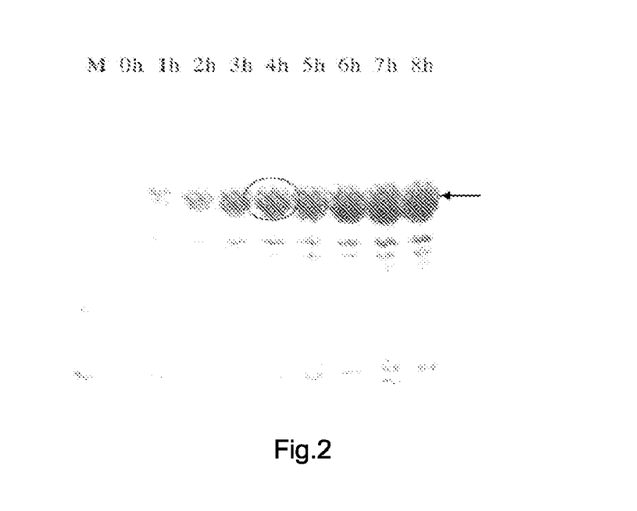
FIG. 2 is the protein expression of EPSP synthase of GR-79 at different time points.

The expression level of E. coli BL21 (DE3) (Promega company) containing pETGR-79 reached the maximum value via IPTG induction at 37° C. for 4 h. The interested protein was soluble protein and the size was about 45 kD as expected (see FIG. 2).

Example 5

Determination of Enzyme Activity and Kinetic Parameters of EPSP

1. Test Methods

Standard curve of inorganic phosphorus: 10 mM inorganic phosphorus was diluted at 1:10, and 0, 1, 2, 3 . . . 20 µl was taken into 1.5 ml Eppendorf tube and milli-Q purified water was added up to 100 µl with mixing, 0.8 ml MAT solution was added with mixing, and then 100 µl 34% SC solution was quickly added with mixing after 3 min, kept at room temperature for 20 min and then the OD660 value was determined. Repeat the operations three times as above. The standard curve of inorganic phosphorus was achieved using the concentration of inorganic phosphorus as abscissa and the OD660 value as ordinate.

1) Enzyme activity test: The crude protein extracted with enzyme was quantified using Coomassie Blue G-250 method (Bradford, 1976). The follow solutions were added into 1.5 ml Eppendorf tube on the ice: 2 µl of 10 mM PEP solution, 2 µl of 10 mM S3P solution, 2 µl of 0.5M HEPES solution, 2 µl of 1 mM $(NH_4)_6MO_7O_{24}.4H_2O$ solution and 12 µl of milli-Q purified water with mixing, bathed at 28° C. for 5 min and 1 µl crude enzyme solution was added into each, tube at intervals and timing, 200 µl MAT solution was added after 2 min at 2s intervals again, color development was performed for 3 min, and then 20 µl of 34% SC solution was added at 2s intervals and quickly mixed well, the color was developed for 20 min at room temperature and finally the OD660 value was determined. The operations of the control were as same as those of the sample except without adding the enzyme solution. The OD660 value of the control tube was subtracted from that of the sample tube, the amount of inorganic phosphorus released from the reaction in mole could be calculated in accordance with the standard curve of inorganic phosphorus, and divided by, reaction time and the amount of enzyme protein to give the activity of the enzyme (U/mg).

2) Determination of half inhibition dose ($IC_{50}$): 0, $10^{-3}$, $10^{-2}$, $10^{-1}$, 1, 10, 100, 500 mM glyphosate was added into the reaction solution as above, and the figure was plotted with the data of the specific activity of the enzyme using the concentration of glyphosate as X axis and the reaction rate as Y axis (U/mg) using logarithmic coordinate.

3) $K_m$ (PEP) assay: The concentration of S3P solution was maintained at 1 mM, the reaction rate of enzyme was determined, in the reaction system as above at different concentration of PEP (0.05, 0.067, 0.1, 0.2, 0.5, 1.0 mM), and the figure was plotted with the values determined using V−v/[S] (Eadic-Hofstee) method.

$K_i$ (glyphosate) assay: The reaction rate of EPSP enzyme was determined at PEP concentration of 66.7, 100, 200, 500 µM and different glyphosate concentration (0, 10, 50, 100 µM). 1/V−1/[S] line was obtained using double log plotting, and a new line was obtained using the slope of each line as ordinate and the concentration of glyphosate as abscissa, the crossing point of the line and X axis was $K_i$ (glyphosate) value.

2. Results

The enzyme activity of GR-79 EPSP was 10.477 U/mg, the measurement of GR-79 EPSP was shown in the table 2:

TABLE 2

| Kinetic parameters of GR-79 EPSP | |
|---|---|
| Kinetic parameters | Value measured |
| $IC_{50}$ (glyphosate; mM) | 12.65 ± 0.012 |
| $K_m$ (PEP; mM) | 0.0792 ± 0.032 |
| $K_i$ (gluphosate; mM) | 0.171 ± 0.002 |
| $K_i/K_m$ | 2.16 |

From the kinetic parameters of GR-79 EPSP, GR-79 EPSP not only had higher glyphosate resistance, but also remained stronger affinity to PEP, and these properties provided the possibility to breed the transgenic crops using GR-79 EPSP.

Example 6

Construction of Plant Expression Vector Containing the Gene of EPSP Synthase with High Glyphosate Resistance The method used to construct a plant expression vector containing the gene of EPSP synthase with high glyphosate resistance is as follows;

A. pBI121 (ClonTech Co., Ltd) and pCAMBIA2301 (Clontech Co., Ltd) were cut with two enzymes, HindIII and EcoRI, and the fragment of pBI121 with p35S-GUS-Nos-ter was ligated into pCAMBIA2301, resulting in the intermediate vector p358-2301-GUS.

B. p35S-2301-GUS and the gene of EPSP synthase artificially synthesized as above were cut with two enzymes, XbaI and Sad, and GUS in p35S-2301-GUS was replaced with EPSP to obtain the plant expression vector containing the gene of EPSP synthase with high glyphosate resistance. The expression vector was then, introduced into *Agrobacterium tumefaciens*, which was subsequently transformed into the model plant tobacco.

Example 7

Transformation Construction of Transgenic Tobacco with High Glyphosate Resistance Using Leaf Disc Protocol (1) A positive clone derived from the YPE selective plate in Example 5 was picked up with sterile toothpick, inoculated into 2 ml YPE liquid ($Sim^r$, $Km^r$) and incubated with shaking at 200 rpm and 28° C. for 24-36 hours;

(2) The culture was centrifuged at 4,000 g at room temperature for 15 min;

(3) The supernatant was discarded and the pellet was suspended into ½ MS liquid medium, diluted to 5-20× the original volume to make the OD600 value be about 0.5;

(4) The sterile leaf of about 2 weeks old was taken, removed the main vein and cut into small pieces of 1 $cm^2$;

(5) The leaves were placed in the prepared bacterial liquid for 2-5 min. The liquid was then blotted with sterile filters. The leaves soaked were placed on MS medium and incubated in the dark at 28° C. for 48 hours;

(6) The leaves were transferred to callus medium (MS+6-BA 1.0 mg/l+NAA.0.1 mg/l+Kan 50 mg/l+carbenicillin 250 mg/l), incubated at 25-28° C., in the light, and the callus tissues were formed after 7-15 days;

(7) The differentiated buds were coming out after about 20 days visibly, they were cut off after grown up, put into the root medium (½ MS+NAA 0.5 mg/L+Kan 25 mg/L) to perform rooting culture, and the roots were observed after about 2-7 days;

(8) The plants were removed when the root systems were large, the solid medium attached was washed off with sterile water, and the plants were transferred into the soil, covered with a glass cover for several days at the beginning days, and the cover was removed after the plants were robust, and then the plants were transferred to the solid medium with 10 mM glyphosate to screen the plant strains with glyphosate resistance;

(9) The plants with glyphosate resistance were confirmed by Southern, Northern and Western blot analysis;

(10) The transgenic plants could grow well in the medium with 20 mM glyphosate, which was confirmed using glyphosate resistance gradient assay in greenhouse.

The invention claimed is:

1. A recombinant or isolated EPSP synthase with high glyphosate resistance having an amino acid sequence at least 95% identical to the amino acid sequence set forth in SEQ ID NO:1.

2. A recombinant or isolated DNA encoding the EPSP synthase of claim 1.

3. A recombinant vector comprising the DNA of claim 2.

4. A host cell transformed with the recombinant vector of claim 3, wherein the host cell is a prokaryotic cell or a eukaryotic cell.

5. The recombinant or isolated DNA of claim 2, wherein the DNA has the sequence set forth in SEQ ID NO:2 or SEQ ID NO:3.

6. A method of making a glyphosate resistant plant, said method comprising introducing the recombinant or isolated DNA of claim 2 into a plant cell and regenerating a glyphosate resistant plant.

* * * * *

SEQUENCE LISTING

```
<160> NUMBER OF SEQ ID NOS: 3

<210> SEQ ID NO 1
<211> LENGTH: 445
<212> TYPE: PRT
<213> ORGANISM: Unknown
<220> FEATURE:
<223> OTHER INFORMATION: From a mixture of organisms

<400> SEQUENCE: 1

Met Ser His Ser Thr Ser Arg Ser Pro Trp Ser Lys Ala Thr Glu Tyr
1               5                   10                  15

His Glu Ala Leu Val Thr Pro Thr Ser Asn Lys Ile Asn Gly Glu Ile
            20                  25                  30

Phe Val Pro Gly Ser Lys Ser Tyr Thr Asn Arg Ala Leu Ile Ile Ala
        35                  40                  45

Ala Leu Ala Glu Gly Thr Ser Thr Leu Lys Gly Ile Leu Lys Ser Asp
    50                  55                  60

Asp Ser Tyr Trp Cys Ile Asp Ala Leu Arg Arg Leu Gly Ile Lys Ile
65                  70                  75                  80
```

Glu Val Ala Glu Glu Thr Val Thr Ile His Gly Cys Gly Gly Lys Trp
                85                  90                  95

Pro Val Gln Ser Ala Glu Leu Phe Ile Gly Ala Ala Gly Thr Ile Ala
            100                 105                 110

Arg Phe Leu Pro Gly Ala Leu Ala Val Ala Gln Gln Gly Glu Trp Ile
        115                 120                 125

Val Asp Gly Val Pro Gln Leu Arg Glu Arg Pro Leu Lys Pro Leu Val
130                 135                 140

Asp Ala Leu Thr Gln Leu Gly Gly Arg Ile Glu Tyr Leu Thr Glu His
145                 150                 155                 160

Pro Gly Leu Pro Leu Arg Val Lys Gly Ala Gly Leu Ser Gly Gln His
                165                 170                 175

Val Arg Val Pro Gly Asn Val Ser Ser Gln Phe Leu Ser Gly Leu Leu
            180                 185                 190

Ile Ala Ser Pro Tyr Ala Ser Glu Ala Val Ser Ile Glu Val Ile Asn
        195                 200                 205

Gly Leu Val Gln Pro Ser Tyr Ile Ala Ile Thr Ile Gln Leu Met Arg
210                 215                 220

Glu Phe Gly Ala Lys Val Glu His Asn Glu Asp Tyr Ser Leu Phe Lys
225                 230                 235                 240

Val Tyr Pro Thr Gly Tyr Gln Gly Arg Asp Thr Ile Leu Glu Ala Asp
                245                 250                 255

Ala Ser Thr Ala Cys Tyr Phe Leu Ser Leu Ala Ala Leu Thr Gly Gly
            260                 265                 270

Thr Ile Gln Val Lys Asn Val Gly Tyr His Ser Tyr Gln Pro Asp Ala
        275                 280                 285

Arg Phe Ile Asp Val Leu Glu Gln Met Gly Cys Glu Val Ile Lys Asn
290                 295                 300

Glu Ser Phe Leu Glu Val Thr Gly Pro Thr Arg Leu Lys Gly Gly Phe
305                 310                 315                 320

Glu Val Asp Met Lys Pro Met Ser Gln Ala Leu Thr Ile Gly Ala
                325                 330                 335

Leu Ala Pro Phe Ala Asp Ala Pro Ile Arg Val Thr Asn Val Ala His
            340                 345                 350

Ile Arg Ala His Glu Ser Asp Arg Ile Ala Val Ile Cys Ser Ser Leu
        355                 360                 365

Gln Gln Met Gly Val Gln Val Glu Glu Arg Glu Asp Gly Phe Thr Ile
370                 375                 380

Tyr Pro Gly Gln Pro Val Gly Thr Thr Leu Asn Pro His Asp Asp His
385                 390                 395                 400

Arg Asn Ala Met Val Phe Gly Leu Leu Gly Val Lys Val Pro His Ile
                405                 410                 415

Arg Ile Val Asp Pro Gly Cys Val Ser Lys Thr Cys Pro Ala Tyr Phe
            420                 425                 430

Glu Glu Leu Gln Lys Phe Gly Ile His Val Glu Tyr Asn
        435                 440                 445

<210> SEQ ID NO 2
<211> LENGTH: 1335
<212> TYPE: DNA
<213> ORGANISM: Unknown
<220> FEATURE:
<223> OTHER INFORMATION: From a mixture of organsims

<400> SEQUENCE: 2

```
atgtcacatt ctacctctag gtccccatgg tccaaggcta ctgagtacca tgaggcactt      60
gtaacaccaa cctcgaacaa gattaacggt gaaatatttg tacctggctc aaagagctat     120
accaatcgag ctctaatcat tgctgcttta gcagagggga cttctacact aagggaata     180 ttaaagagtg atgattccta ctggtgtatt gatgccttaa ggaggcttgg cattaagatc     240
gaggttgccg aagagacggt caccattcat ggctgtggag gaaaatggcc agttcaatct     300
gcagagcttt ttattggggc tgcaggtacc attgcccgct ccttccagg  agccttagct     360 gttgcccagc aaggggagtg gatcgtagat ggggttccac aactgcgaga agaccatta     420 aaacctttag tggatgcctt aactcagctt ggtggtagaa tagagtatct gactgagcat     480
ccgggtctgc ctttacgagt aaaggggggca ggtctaagtg gacagcatgt aagggtgcca    540
ggaaatgtct ctagccaatt tttaagtggt ttattaatcg ccagtcctta tgcctcagaa     600
gctgtcagca ttgaggtaat caatggactc gttcaaccgt cttacattgc cattacgatt     660
cagttaatga gagaatttgg tgccaaagtg gagcataatg aggattacag tctctttaag     720
gtttacccta ctggatacca aggtcgtgat accatacttg aggcagatgc ttcaacagcc     780 tgctatttt  tatccttagc agcgttaact ggaggtacca tccaggtgaa gaatgttggc     840
tatcattcgt atcagccaga tgctcgtttc attgatgtgt tagagcaaat gggctgtgaa     900
gtgattaaga tgagtcatt  cctagaggtt acagcccaa cccgattaaa gggtggcttc      960
gaggtggata tgaagcctat gtctgaccaa gcgttgacca taggcgcatt agctcctttt    1020
gcagatgcac cgattcgggt aaccaatgtc gctcacatta gggctcatga gtcagaccgg    1080
atagctgtta tttgttcctc gttacagcag atgggagttc aggtagagga gagagaggat    1140
ggctttacta tctatccagg tcagccagtg ggtacaacgc ttaatcctca tgatgatcat    1200
cgtaatgcaa tggtattcgg tttacttgga gtaaaagtac cacatattag aatagtcgat    1260
ccgggttgtg tatctaagac ctgcccagcc tattttgaag agctgcagaa gtttggaata    1320
catgtggagt ataat                                                    1335
```

<210> SEQ ID NO 3
<211> LENGTH: 1335
<212> TYPE: DNA
<213> ORGANISM: Artificial
<220> FEATURE:
<223> OTHER INFORMATION: synthetic construct

<400> SEQUENCE: 3

```
atgtcacatt ctacctctag gtccccatgg tccaaggcta ctgagtacca tgaggccctt      60
gtgaccccaa cctcgaacaa gattaacggt gagatcttcg tgcctggctc aaagagctac     120
accaaccgcg ctctcatcat tgctgctttg gccgagggga cttctaccct aagggaatc     180 ttgaagagtg atgattccta ctggtgcatt gatgccttga ggaggcttgg cattaagatc     240
gaggttgccg aggagaccgt gaccattcat ggctgcggag gaaagtggcc agttcaatct     300
gccgagcttt tcattggggc tgccggtacc attgcccgct ccttccagg  agccttggct     360 gttgcccagc aaggggagtg gatcgtggat ggggttccac aactccgcga agaccattg     420 aagcctttgg tggatgcctt gactcagctt ggtggtagaa tcgagtacct cactgagcat     480
ccgggtctcc ctttgcgcgt gaagggagct ggtctcagtg gacagcatgt gagggtgcca    540
ggaaacgtgt ctagccaatt cttgagtggt ttgttgatcg ccagtcctta cgcctcagag    600
gctgtgagca ttgaggtgat caacggactc gttcaaccgt cttacattgc cattaccatt    660
cagttgatga gagagttcgg tgccaaggtg gagcataacg aggattacag tctcttcaag    720
```

```
gtttacccta ctggatacca aggtcgtgat accatccttg aggccgatgc ttcaaccgcc      780
tgctacttcc tctccttggc cgcgttgact ggaggtacca tccaggtgaa gaacgttggc      840
taccattcgt accagccaga tgctcgtttc attgatgtgt tggagcaaat gggctgcgag      900
gtgattaaga acgagtcatt cctcgaggtt accggcccaa cccgcttgaa gggtggcttc      960
gaggtggata tgaagcctat gtctgaccaa gccttgacca tcggcgcctt ggctcctttc     1020
gccgatgccc cgattcgcgt gaccaacgtc gctcacatta gggctcatga gtcagaccgc     1080
atcgctgtta tttgctcctc gttgcagcag atgggagttc aggtggagga gagagaggat     1140
ggcttcacta tctacccagg tcagccagtg ggtaccaccc ttaaccctca tgatgatcat     1200
cgtaacgcca tggtgttcgg tttgcttgga gtgaaggtgc cacatattag aatcgtggac     1260
ccgggttgcg tgtctaagac ctgcccagcc tacttcgaag agctccagaa gttcggaatc     1320
catgtggagt acaac                                                      1335
```